(12) United States Patent
Ono

(10) Patent No.: US 7,300,154 B2
(45) Date of Patent: Nov. 27, 2007

(54) OPHTHALMOLOGIC IMAGE TAKING APPARATUS

(75) Inventor: Shigeaki Ono, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 777 days.

(21) Appl. No.: 10/703,792

(22) Filed: Nov. 6, 2003

(65) Prior Publication Data

US 2004/0095554 A1  May 20, 2004

(30) Foreign Application Priority Data

Nov. 11, 2002  (JP)  ............................. 2002-326938

(51) Int. Cl.
*A61B 3/14* (2006.01)
*A61B 3/10* (2006.01)
*A61B 3/02* (2006.01)

(52) U.S. Cl. ...................... 351/206; 351/211; 351/221; 351/237; 351/243

(58) Field of Classification Search ................ 359/206, 359/210, 211, 216, 220, 221, 228, 237, 243
See application file for complete search history.

(56) References Cited

U.S. PATENT DOCUMENTS 4,412,728 A   11/1983  Skane et al. ................ 351/206
5,557,321 A   9/1996   Kohayakawa et al. ........ 348/78
6,325,511 B1  12/2001  Mizuochi ..................... 351/206
6,327,375 B1  12/2001  Matsumoto et al.
6,585,374 B2* 7/2003   Matsumoto .................. 351/206

OTHER PUBLICATIONS

EPO Communication (Mar. 8, 2004) w/EPO Search Report (Feb. 26, 2004).

* cited by examiner

*Primary Examiner*—Ricky Mack
*Assistant Examiner*—Brandi Thomas
(74) *Attorney, Agent, or Firm*—Morgan & Finnegan LLP

(57) ABSTRACT

Provided is an ophthalmologic image taking apparatus with which an image of the eye to be examined can be taken with an appropriate light intensity and at an appropriate gain. In the case where an observation of an eye to be examined is conducted when it is detected that an image taking switch is turned on, an image taking light source emits light after a lapse of a predetermined time. The predetermined time is a time required to completely switch a gain from a gain obtained by AGC to a fixed gain and a time which is not influenced by blinking of the eye to be examined.

5 Claims, 8 Drawing Sheets

OPHTHALMOLOGIC IMAGE TAKING APPARATUS

BACKGROUND OF THE INVENTION

1. Field of the Invention

The present invention relates to an ophthalmologic image taking apparatus that picks up an image of an eye to be examined in an ophthalmologic clinic and the like.

2. Related Background Art

Up to now, there has been known an ophthalmologic image taking apparatus in which an image of an eye to be examined is picked up using an image pickup device represented by a CCD and converted into a video signal, thereby conducting an observation of the eye to be examined and image taking thereof. In such an ophthalmologic image taking apparatus, an output signal from the image pickup device is electrically amplified in order to conduct control by which the image of the eye to be examined always becomes a suitable video signal.

In the case where infrared fluorescent image taking is conducted, an eye fundus cannot be observed through an optical finder. Therefore, two kinds of cameras for observation and image taking are prepared and used with gains thereof being set to be different from each other. However, using two television cameras causes the ophthalmologic image taking apparatus to become complicated and further increasing a cost thereof.

In order to solve the above-mentioned problem, an ophthalmologic image taking apparatus that conducts the observation of the eye to be examined and the image pickup thereof using a single image pickup device is disclosed in Japanese Patent Application Laid-Open Nos. H9-262211 and H10-234671, or the like.

However, there is no description with respect to gain setting in Japanese Patent Application Laid-Open No. H9-262211. In addition, in the ophthalmologic image taking apparatus disclosed in Japanese Patent Application Laid-Open No. H10-234671, an ND filter is changed in accordance with an image taking mode to change the light intensity for image taking in order to conduct control by which an image of the eye to be examined becomes an image of a suitable video signal.

In the case of an observation using visible fluorescence or infrared fluorescence, the brightness of the eye to be examined changes according to a circulating state of a fluorescer. In particular, because the change in the brightness of the eye to be examined is remarkable in an initial image, auto gain control (AGC) is operated. Therefore, even if the brightness of the eye to be examined, that is, even if the light intensity for observation changes, it is desirable to conduct the control such that the image of the eye to be examined always becomes an image of a suitable video signal.

On the other hand, because a light emission time of an image taking light source used in the case of image taking is a short time of several milliseconds, even if the AGC is executed, the change in the brightness of the eye to be examined cannot be attained accordingly. Therefore, instead of the gain obtained by the AGC, a fixed gain is used in image taking and the light intensity for image taking is adjusted according to the brightness of the eye to be examined, thereby making it possible to conduct the control by which the image of the eye to be examined becomes an image of a suitable video signal.

However, in the case where the AGC is switched to the fixed gain control, a predetermined time is required to stabilize the gain. Such predetermined time is caused by, in the case where an apparatus main body and a television camera unit are used in combination and switching between the gain obtained by the AGC and the fixed gain is controlled using a communication port such as RS-232C, a communication time and a response time of a gain circuit. If the image taking light source emits light to conduct image taking with a state in which the gain control is not completely switched, the brightness is saturated or an image becomes dark. That is, a suitable video signal is not captured.

In contrast to this, even in the case where the fixed gain is switched to the gain obtained by the AGC, a predetermined time is required to stabilize the gain. In this case, in addition to a cause of a time delay in the case where the gain obtained by the AGC is switched to the fixed gain, a delay of a time corresponding to at least a frame or a field is caused because the gain is determined based on a video signal of the picked up image of the eye to be examined. Therefore, a time is further required to converge the gain. If moving image recording of the eye to be examined is conducted under a state in which the gain control is not completely switched, the brightness is saturated or an image becomes dark. That is, a suitable video signal is not captured.

SUMMARY OF THE INVENTION

An object of the present invention is to solve the above-mentioned problems and to provide an ophthalmologic image taking apparatus capable of conducting an observation of an eye to be examined, moving image recording thereof, and still image taking thereof using a single television camera.

To achieve the above-mentioned object, an ophthalmologic image taking apparatus according to the present invention includes: an illumination optical system that has an observation illumination light source and an image taking illumination light source and projects one of an observation illumination light and an image taking illumination light to an eye to be examined; image pickup means for receiving a reflection light from the eye to be examined to pick up the reflection light as an image of the eye to be examined; amplifying means for amplifying a video signal from the image pickup means; image capturing means having a plurality of operational modes for obtaining an output signal from the amplifying means as an image of the eye to be examined; gain control means for controlling a gain of the amplifying means; and a mode switch for switching among the operational modes of the image capturing means, in which the gain control means has a first gain setting mode for changing the gain in accordance with the video signal from the image pickup means and a second gain setting mode for setting the gain to a fixed gain.

Further objects and structures of the present invention will be apparent from embodiments described later.

DESCRIPTION OF THE PREFERRED EMBODIMENTS

Figure 1:
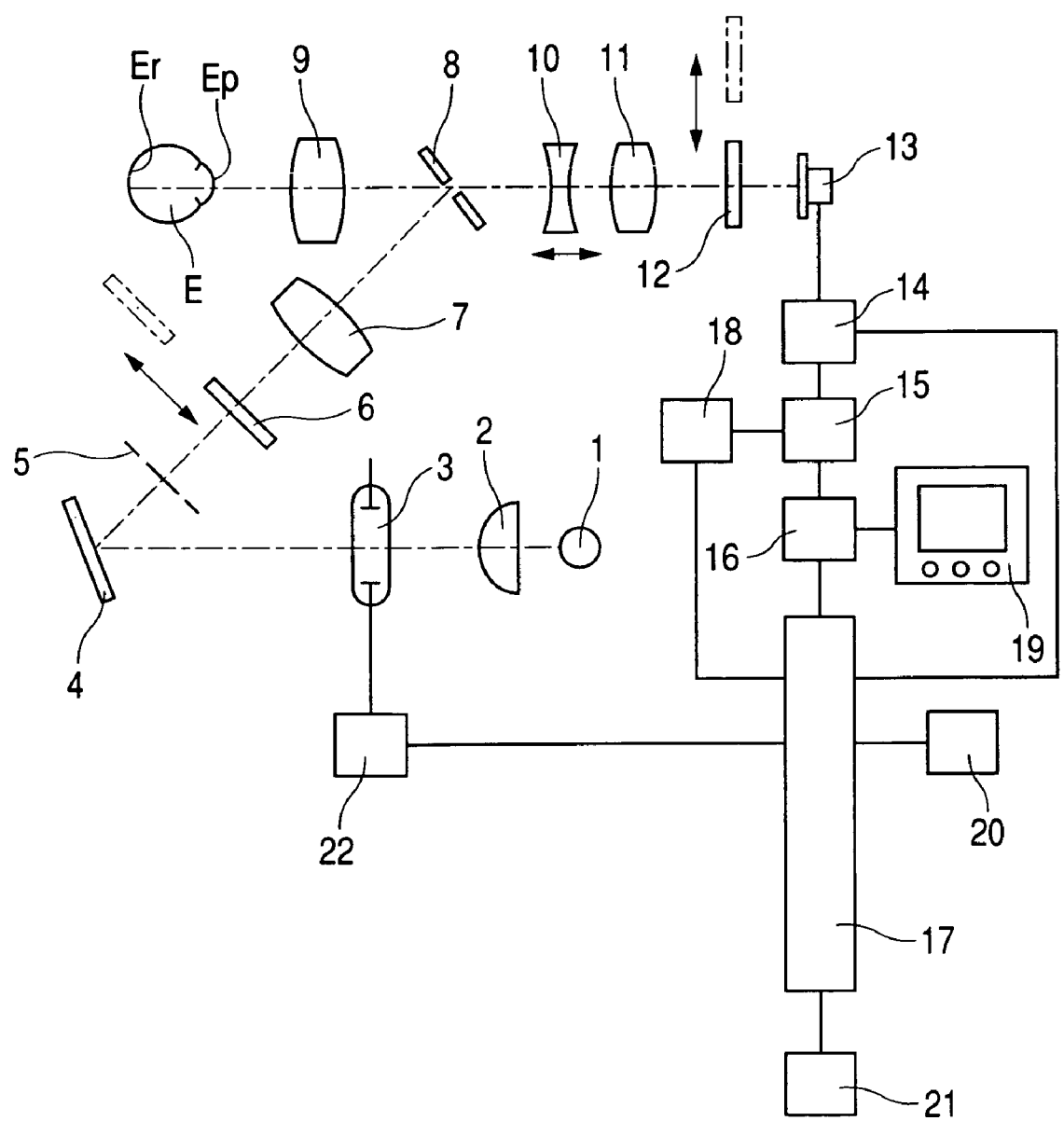
FIG. 1 is a structural diagram of an eye fundus camera according to a first embodiment.

The present invention will be described in detail with reference to embodiments shown in the drawings.

FIG. 1 is a structural diagram of an eye fundus camera according to a first embodiment. On an optical path of an eye fundus illumination optical system from an observation light source 1 to an eye to be examined E, a condenser lens 2, an image taking light source 3, a mirror 4, a diaphragm 5 having a ring-shaped opening, an infrared fluorescent exciter filter 6 located so as to be insertable to the optical path, 7, a relay lens 7, a holed mirror 8, and an objective lens 9 are disposed in the stated order. In addition, in an eye fundus image taking optical system in the rear of the holed mirror 8, a focusing lens 10, an image taking lens 11, an infrared fluorescent barrier filter 12 that blocks excitation light and transmits only fluorescence, and is insertable to the optical path, and an image pickup device 13 are disposed in the stated order.

Also, the output of the image pickup device 13 is connected with a system control unit 17 through a storage charge reading unit 14, an amplifying unit 15, and an image signal processing unit 16. Further, the output of the storage charge reading unit 14 is directly connected with the system control unit 17, and the output of the amplifying unit 15 is connected with the system control unit 17 through a gain control unit 18. Further, the output of the image signal processing unit 16 is connected with a display unit 19.

Further, the system control unit 17 is connected with image record means 20 composed of a hard disk, an MO, a Zip, a Jazz, a CD-R/RW, DVD-RAM, DVD-R/RW, a semiconductor memory, or the like, an image taking switch 21, and an image taking light source control unit 22 that controls the image taking light source 3.

A light flux emitted from the observation light source 1 transmits through the condenser lens 2 and the image taking light source 3 and is reflected on the mirror 4. The reflected light on the mirror 4 transmits through the diaphragm 5 having the ring-shaped opening, the infrared fluorescent exciter filter 6, and the relay lens 7 and is reflected on the peripheral portion of the holed mirror 8. The reflected light on the peripheral portion of the holed mirror 8 transmits through the objective lens 9 and an eye pupil Ep of the eye to be examined E to illuminate an eye fundus Er. An eye fundus image captured by the illumination transmits through the eye pupil Ep of the eye to be examined E, the objective lens 9, the hole portion of the holed mirror 8, the focusing lens 10, the image taking lens 11, and the infrared fluorescent barrier filter 12 and imaged on the image pickup device 13.

The storage charge reading unit 14 reads a storage charge which is photoelectric-converted by the image pickup device 13 and stored therein and clears the stored charge in succession. A signal corresponding to the read storage charge is outputted from the storage charge reading unit 14 to the image signal processing unit 16 through the amplifying unit 15. The image signal processing unit 16 conducts processing on the signal, which is required for outputting an observation image to the display unit 19, and causes the display unit 19 to display the observation image.

Meanwhile, the system control unit 17 controls the gain control unit 18 based on the AGC to enable an appropriate eye fundus observation to be conducted even if the light intensity of the observation light source 1 is not reset for each time when the brightness of the eye fundus Er of the eye to be examined E changes.

Figure 2:
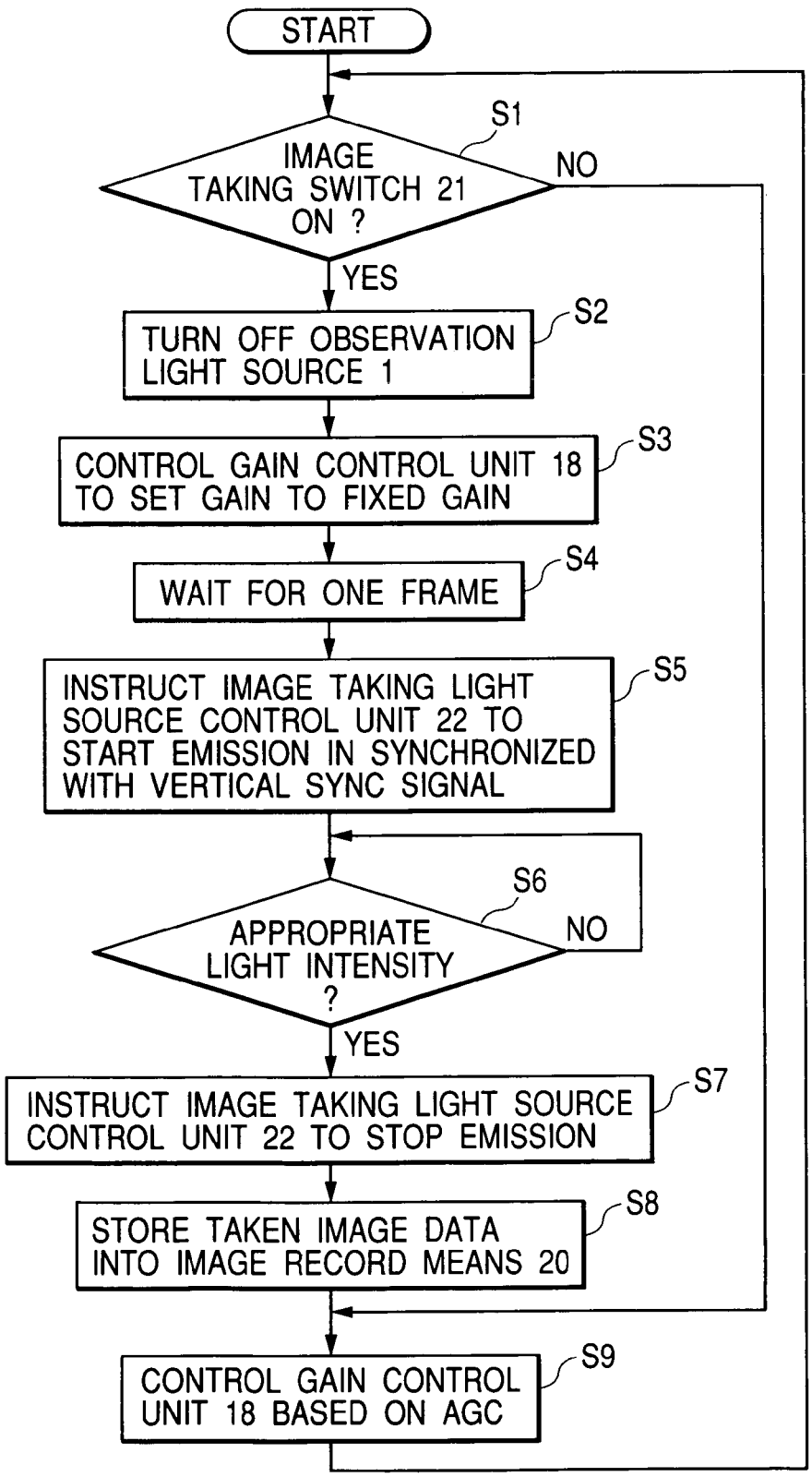
FIG. 2 is a flow chart showing an operation of a system control unit in the first embodiment.

FIG. 2 is a flow chart showing the operation of the system control unit 17 upon image taking. An operator conducts alignment operation while observing a video on the display unit 19. First, in Step S1, when the image taking switch 21 is turned on by the operator after the alignment is completed, the system control unit 17 detects the input of the image taking switch 21. In Step S2, the observation light source 1 is turned off. In Step S3, the gain control unit 18 is controlled to set the gain from the gain obtained by the AGC to the fixed gain.

Figure 3:
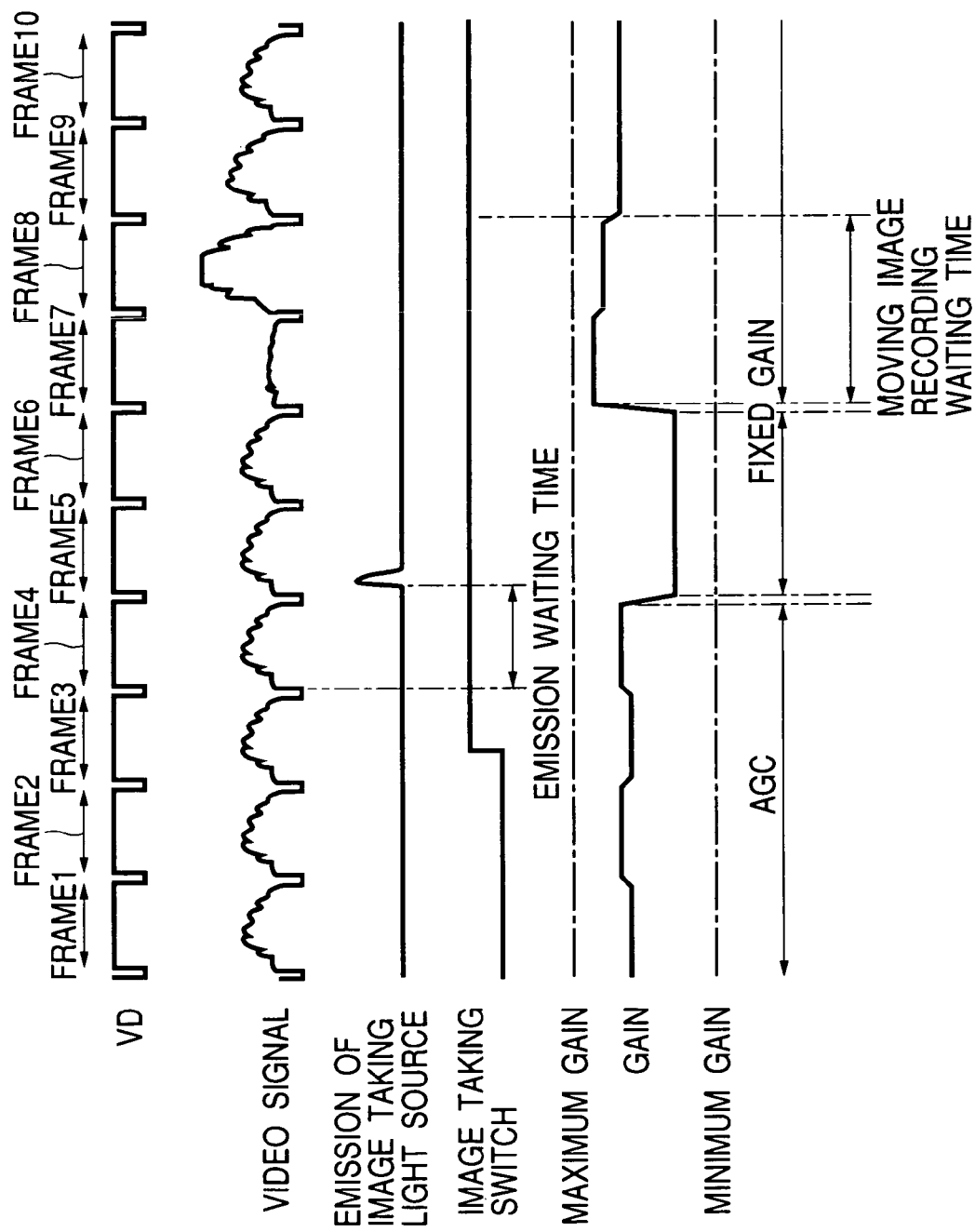
FIG. 3 is a time chart.

Subsequently, in Step S4, a waiting time corresponding to one frame is allowed to elapse. The waiting time is an emission waiting time as shown in FIG. 3. The emission waiting time for one frame is a time required to stabilize the gain of the amplifying unit 15 after setting of the gain control unit 18 is changed. However, if the emission waiting time is too long, the operation is easily influenced by blinking of the eye to be examined E. Therefore, a time corresponding to about four or less frames is desirable. In addition, the reason why a frame is set as a unit is because the storage charge reading unit 14 conducts frame reading. Thus, in the case of the field reading, one to eight fields may be set.

Subsequently, in Step S5, the system control unit 17 outputs an emission start instruction to the image taking light source unit 22 in synchronized with a vertical synchronization signal as shown in FIG. 3 to emit a light flux from the image taking light source 3. The light flux emitted from the image taking light source 3 is projected as the eye fundus image of the eye to be examined E to the image pickup device 13. The image pickup device 13 stores a charge obtained by photoelectric conversion and holds the charge. In addition, the system control unit 17 transmits a signal indicating the emission of the image taking light source 3 to the storage charge reading unit 14. The storage charge reading unit 14 starts to read the storage charge in response to the signal from the system control unit 17.

Further, in Step S6, it is determined whether or not the light intensity of the image taking light source 3 reaches an appropriate light intensity. When the light intensity reaches the appropriate light intensity, the operation advances to Step S7. In Step S7, an emission stop instruction for the image taking light source 3 is outputted to the image taking light source unit 22 to stop the emission of the image taking light source 3. A video signal read by the storage charge reading unit 14 is amplified by the amplifying unit 15, converted into a digital signal by an A/D converter which is not shown through the image signal processing unit 16, and then inputted to the system control unit 17.

In Step S8, the digital video signal converted by the A/D converter is recorded on the image record means 20. After that, because the operational mode is returned to the eye fundus observation mode, the gain control unit 18 is controlled based on the AGC in Step S9. Then, the operation returns to Step S1.

According to this embodiment, the control is conducted so as to wait for one frame in Step S4 until the gain of the amplifying unit 14 is stabilized after the gain control unit 18 is controlled to set the gain to the fixed gain in Step S3. Alternately, the following control may be conducted. That is, the system control unit 17 monitors a video signal inputted from the image signal processing unit 16. When it is detected that the gain control unit 18 is controlled to switch the gain from the gain obtained by the AGC to the fixed gain, the system control unit 17 outputs the emission start instruction to the image taking light source unit 22 in synchronized with the vertical synchronization signal to emit light from the image taking light source 3.

Figure 4:
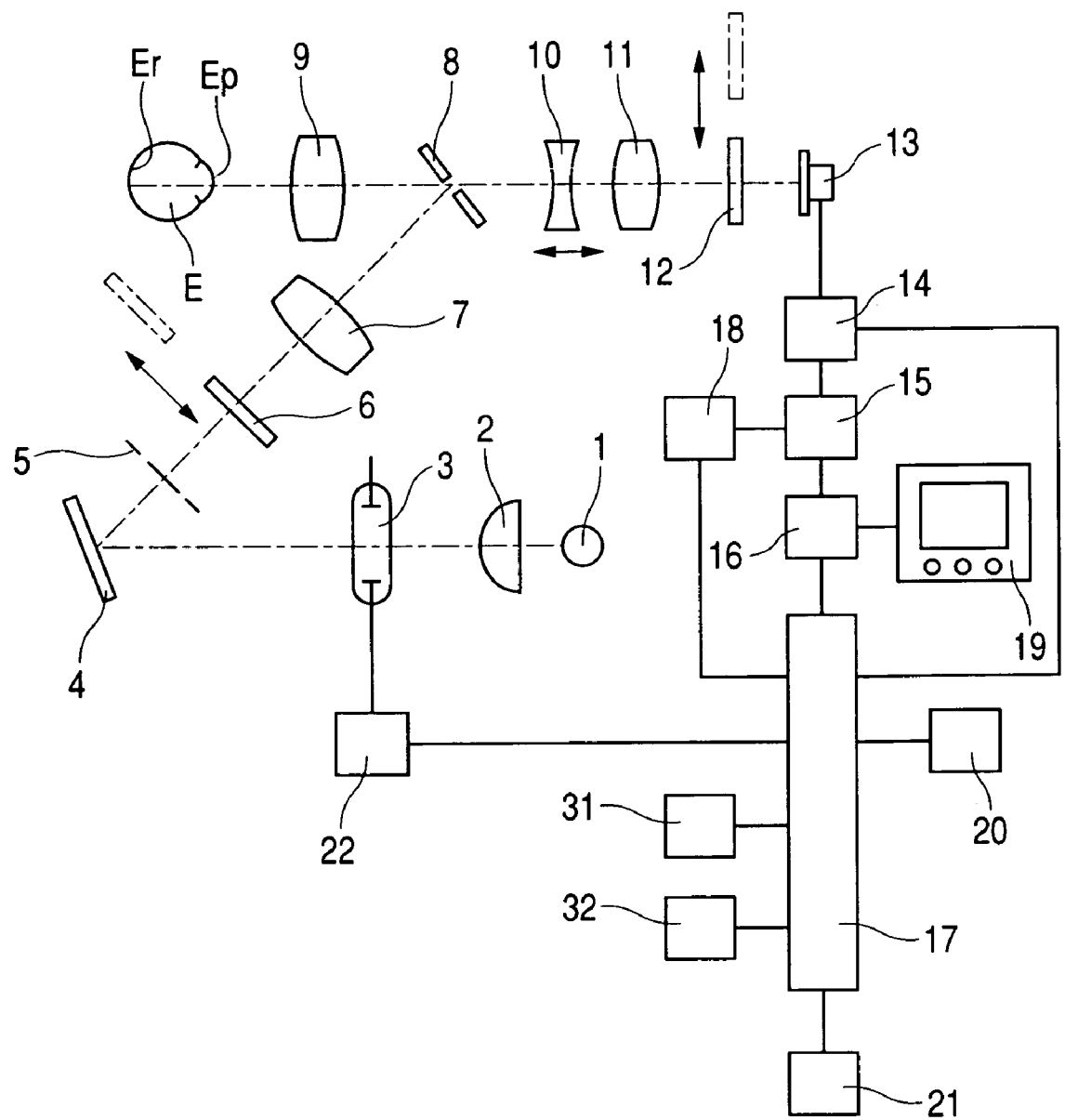
FIG. 4 is a structural diagram of an eye fundus camera according to a second embodiment.

FIG. 4 is a structural diagram of an eye fundus camera according to a second embodiment. The same reference numerals are provided to the same units as in the first embodiment. In this embodiment, the system control unit 17 is further connected with a moving image recording time setting unit 31 and a timer switch 32.

Figures 5, 5A:
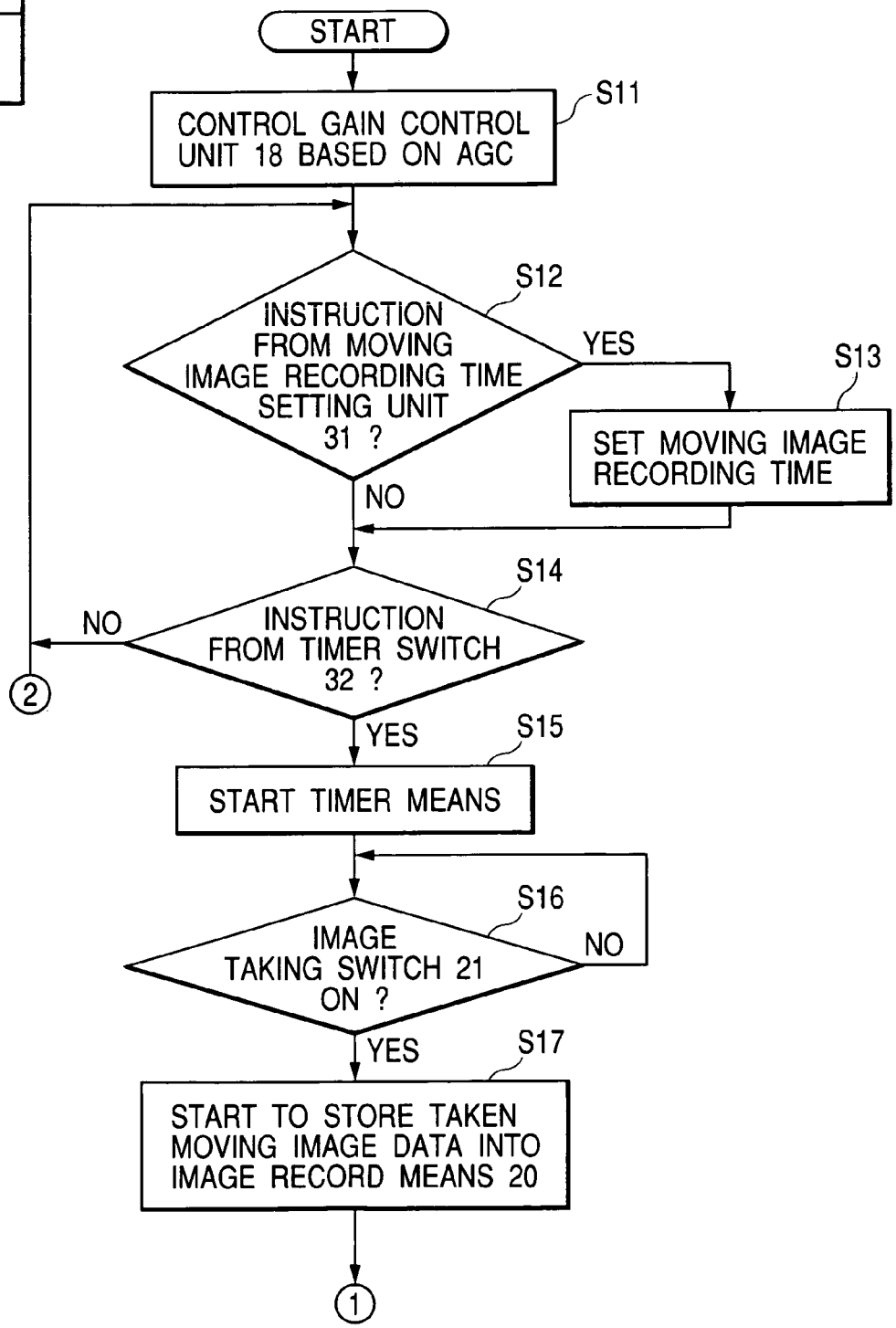
FIG. 5 is comprised of FIGS. 5A and 5B are flow charts showing an operation of a system control unit in the second embodiment.
Figure 5B:
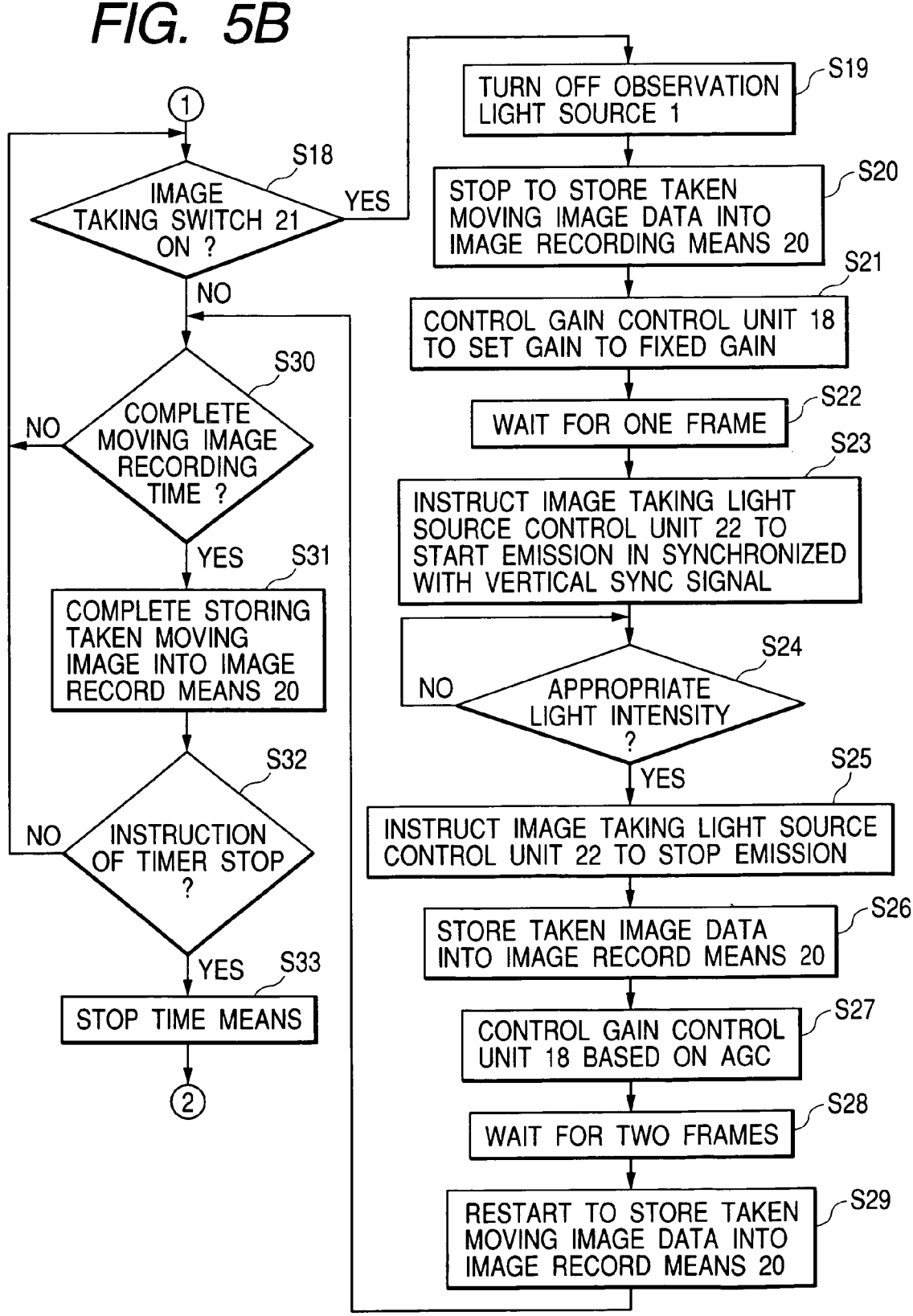

FIGS. 5A and 5B are flow charts showing an operation of the system control unit 17 in this embodiment. The eye fundus camera is set to the eye fundus observation mode which is an initial setting mode. First, in Step S11, the gain control unit 18 is controlled based on the AGC. Accordingly, even if the light intensity of the observation light source 1 is not reset for each time when the brightness of the eye fundus Er of the eye to be examined E changes, an appropriate eye fundus observation can be conducted.

Subsequently, in Step S12, it is determined whether or not an instruction from the moving image recording time setting unit 31 is inputted. When it is determined that the instruction is inputted, the operation advances to Step S13. In Step S13, a moving image recording time for a moving image recording mode is set, and then the operation advances to Step S14. When it is determined in Step S12 that the instruction from the moving image recording time setting unit 31 is not inputted, a default setting value is set and the operation advances to Step S14. Note that a default moving image recording time in this embodiment is set to five minutes.

In Step S14, it is determined whether or not an instruction from the timer switch 32 is inputted. When it is determined that the instruction is not inputted, the operation returns to Step S12 again. On the other hand, when it is determined that the instruction is inputted, the operation advances to Step S15 and timer means which is not shown in the system control unit 17 is started. The timer means described here is a timer that measures a time from the start of an intravenous injection in the case of the visible and infrared fluorescent image taking. It is determined that the observation and the image taking are conducted for a patient during a period from the start of measurement with the timer means to the end thereof.

Subsequently, in Step S16, it is determined whether or not the input of the image taking switch 21 is detected. When the input of the image taking switch 21 is detected, the operation advances to Step S17. Therefore, the operational mode is changed to the moving image recording mode and storing of moving image data into the image record means 20 is started. With respect to the moving image recording in this case, it is possible to reduce the amount of data by data compression processing such as MPEG. Note that, in the moving image recording mode, the gain control unit 18 is controlled based on the AGC.

Subsequently, after the moving image recording starts, an operator conducts alignment operation while observing a video on the display unit 19. Then, in Step S18, when the image taking switch 21 is turned on again by the operator after the alignment is completed, the operation advances to Step S19. In Step S19, the observation light source 1 is turned off by the system control unit 17. Further, in Step S20, the storing of the moving image data into the image record means 20 is stopped. Furthermore, in Step S21, the gain control unit 18 is controlled to set the gain from the gain obtained by the AGC to the fixed gain. After that, a waiting time corresponding to one frame is allowed to elapse in Step S22. The waiting time is the emission waiting time as shown in FIG. 3.

Subsequently, in Step S23, the system control unit 17 outputs the emission start instruction to the image taking light source unit 22 in synchronized with the vertical synchronization signal as shown in FIG. 3 to emit the light flux from the image taking light source 3. The light flux emitted from the image taking light source 3 is reflected on the eye fundus Er of the eye to be examined E and projected as the eye fundus image to the image pickup device 13. The image pickup device 13 stores a charge obtained by photoelectric conversion and holds the charge. The system control unit 17 transmits the signal indicating the emission of the image taking light source 3 to the storage charge reading unit 14. The storage charge reading unit 14 starts to read the storage charge in response to the signal from the system control unit 17.

Then, in Step S24, it is determined whether or not the light intensity of the image taking light source 3 reaches the appropriate light intensity. When the light intensity reaches the appropriate light intensity, the operation advances to Step S25. In Step S25, the emission stop instruction is outputted to the image taking light source control unit 22 to stop the emission of the image taking light source 3. A read video signal is amplified by the amplifying unit 15, converted into a digital signal by the A/D converter through the image signal processing unit 16, and then inputted to the system control unit 17. After that, in Step S26, the digital video signal converted in Step S25 is recorded on the image record means 20 and then the gain control unit 18 is controlled based on the AGC in Step S27.

Subsequently, in Step S28, a waiting time corresponding to two frames is allowed to elapse. The waiting time is the moving image recording waiting time as shown in FIG. 3. After that, in Step S29, the storing of the moving image data into the image record means 20 is restarted and the operational mode is changed to the moving image recording mode. The moving image recording waiting time for two frames in Step S28 is a sum of a time required to stabilize the gain of the amplifying unit 15 after setting of the gain control unit 18 is changed and a time required to determine the gain from the video signal inputted to the system control unit 17. Due to the waiting time corresponding to two frames, i.e., the moving image recording waiting time in Step S28, recording of an image of a video signal amplified by an erroneous gain as a moving image on the image record means 20 can be prevented.

Thus, when the moving image taking is completed or when the input of the image taking switch 21 is not detected in Step S18, it is determined in Step S30 whether or not the moving image recording is completed. That is, it is determined whether the moving image recording time or the default moving image recording time which is set in Step S13 is completed. When the moving image recording time or the default moving image recording time is not attained, the operation returns to Step S18 and the presence of the input of the image taking switch 21 is checked. On the other hand, when the moving image recording time or the default moving image recording time is attained, the storing of the moving image data into the image record means 20 is attained and the operational mode is changed from the moving image recording mode to the eye fundus observation mode.

Further, in Step S32, it is determined whether or not an instruction of timer stop from the timer switch 32 is inputted.

When the instruction of timer stop is not inputted, the operation returns to Step S18 and the presence of the input of the image taking switch 21 is checked. On the other hand, when the instruction of timer stop from the timer switch 32 is inputted, the timer means in the system control unit 17 is stopped in Step S33, so that the image taking for a patient is completed. Then, the operation returns to Step S12 and the presence of the input of the instruction from the moving image recording time setting unit 31 is checked again.

Figure 6:
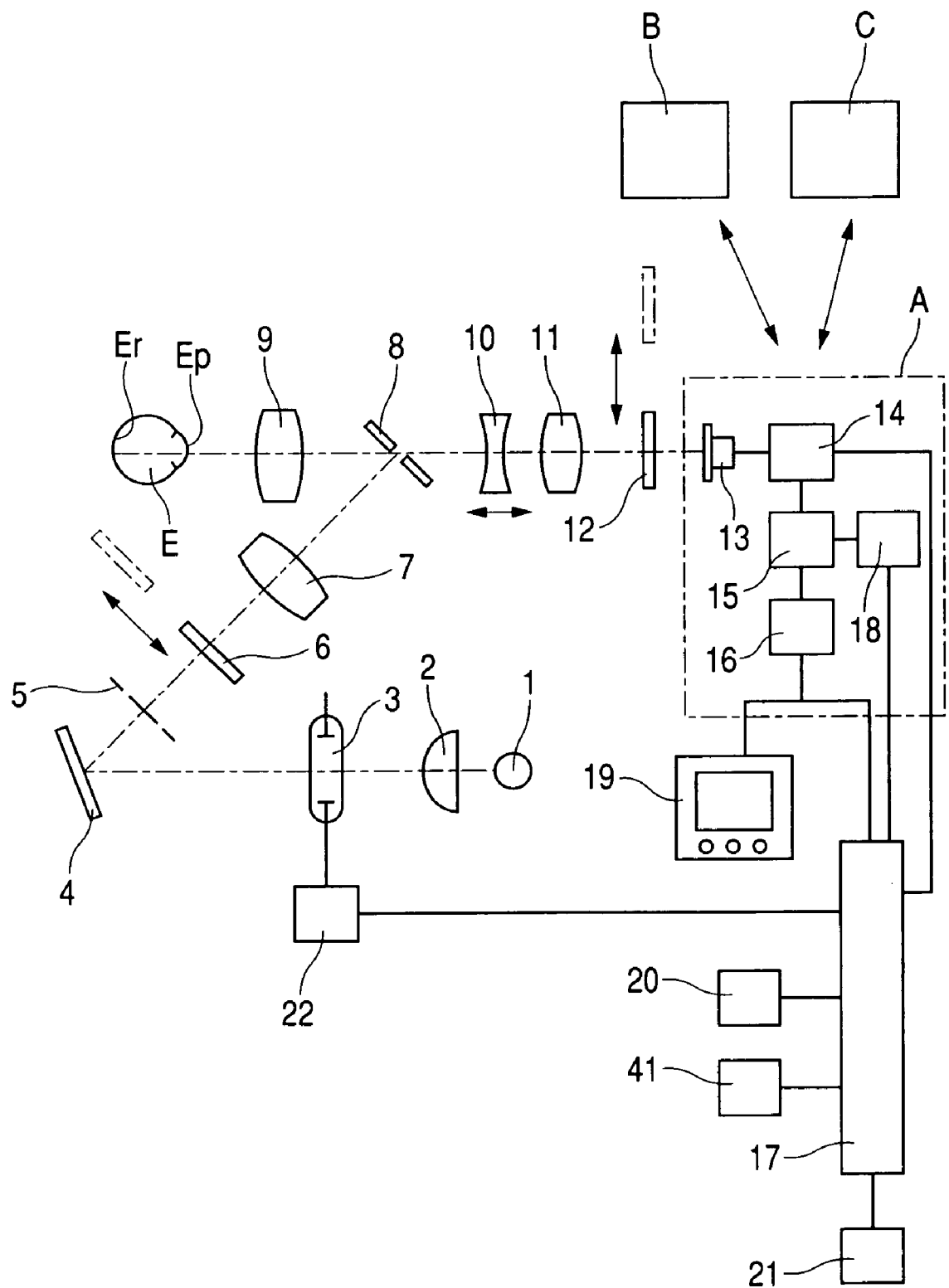
FIG. 6 is a structural diagram of an eye fundus camera according to a third embodiment.

FIG. 6 is a structural diagram of an eye fundus camera according to a third embodiment. A television camera unit "A" which is composed of the image pickup device 13, the storage charge reading unit 14, the amplifying unit 15, the gain control unit 18, and the image signal processing unit 16 is disposed at the imaging position in the eye fundus image taking optical system. The television camera unit "A" is connected with the system control unit 17 and the display unit 19. The television camera unit "A" is constructed so as to be exchangeable for a television camera unit "B" or a television camera unit "C". In addition, the system control unit 17 is connected with an emission waiting time setting unit 41 for the image taking light source 3.

Figure 7:
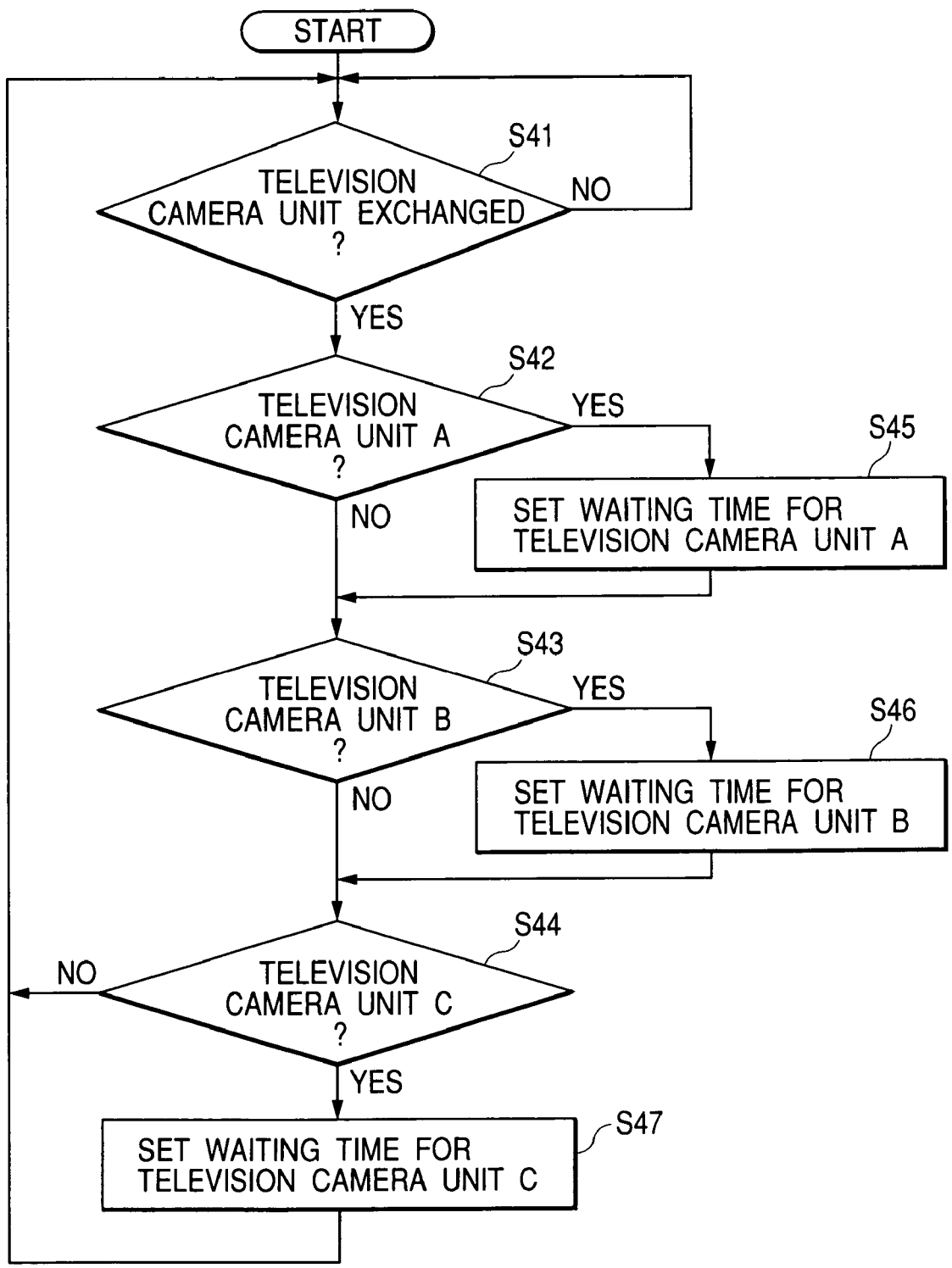
FIG. 7 is a flow chart showing an operation of a system control unit in the third embodiment.

FIG. 7 is a flow chart showing an operation of the system control unit 17 in the case where a television camera unit is exchanged for another television camera unit. First, in Step S41, it is determined whether or not the television camera unit is exchanged for another television camera unit. When it is determined that the television camera unit is exchanged for another television camera unit, for which one of the television camera units "A" to "C" is exchanged is determined in Steps S42, S43, and S44. In Steps S45, S46, and S47, the emission waiting time of the image taking light source corresponding to the determined television camera unit is set.

The emission waiting time of the image taking light source is set to a time corresponding to one frame in Step S4 shown in FIG. 2 in the first embodiment. In addition, in the second embodiment, the emission waiting time of the image taking light source is set to a time corresponding to one frame in Step S22 shown in FIG. 4. However, because a time required to stabilize the gain after the AGC is switched to the fixed gain control is changed according to a type of the television camera unit and a lot thereof, it is possible to separately set the emission waiting time.

The emission waiting time of the image taking light source may be set as follows. That is, a parameter for the emission waiting time is provided for each of television camera units and then the emission waiting time is set for the system control unit 17 by parameter communication using a communication unit such as RS-232C when a television camera unit is attached to the eye fundus camera. In addition, it is possible to set an emission waiting time for each television camera unit by the emission waiting time setting unit 41 for the image taking light source 3.

As described above, according to an ophthalmologic image taking apparatus of the present invention, there are the following advantages.

(1) In the case where the observation of the eye to be examined is conducted when it is detected that the image taking switch is turned on, the image taking light source emits light after a lapse of a predetermined time. The predetermined time is a time required to completely switch the gain from the gain obtained by the AGC to the fixed gain and is a time, which is not influenced by blinking of the eye to be examined. The image of the eye to be examined can be taken with an appropriate light intensity and at an appropriate gain.

(2) In the case where the observation of the eye to be examined is conducted when it is detected that the image taking switch is turned on, it is ensured that the gain is completely switched from the gain obtained by the AGC to the fixed gain by observing the image of the eye to be examined which is irradiated by the observation illumination light source. Thus, the image of the eye to be examined can be taken with the appropriate light intensity and at the appropriate gain.

(3) In the case where the image taking is conducted when the moving image of the eye to be examined which is irradiated by the observation illumination light source is recorded and it is detected that the image taking switch is turned on, the image taking light source emits light after a lapse of a predetermined time. The predetermined time is a time required to completely switch the gain from the gain obtained by the AGC to the fixed gain. Both the moving image of the eye to be examined and the still image thereof can be taken with the appropriate light intensity at the appropriate gain.

(4) It is detected that the recording of the still image of the eye to be examined is completed and the moving image recording is restarted after a lapse of a predetermined time. Accordingly, when the gain is switched from the gain obtained by the AGC to the fixed gain, recording of the moving image of the eye to be examined, which is obtained with an inadequate light intensity and at an inadequate gain before the gain is stabilized can be prevented. Further, a file size of the moving image can be reduced.

(5) The television camera unit which includes the image pickup unit, the amplifying unit, and the gain control unit is attachable. Further, a predetermined time required to emit light from the image taking light source can be changed and switching between the moving image recording mode and the observation mode is possible by the attached television camera unit. Therefore, when it is detected that the image taking switch is turned on in the observation mode, the operational mode becomes the moving image recording mode and the moving image recording is conducted for only a preset time. When it is detected that the image taking switch is turned on in the moving image recording mode, the image taking light source emits light and the still image recording mode is conducted. Thus, both the moving image recording and the still image recording can be conducted by using the image taking switch, so that an operation becomes easy. In addition, the recording can be conducted by only the single switch, so that the ophthalmologic image taking apparatus can be constructed at low cost.

(6) Because the illumination optical system includes the visible or infrared fluorescent exciter filter and the observation image taking optical system includes the visible or infrared fluorescent barrier filter, the visible or infrared fluorescent observation image taking is possible. In the case where the present invention is applied to an ophthalmologic image taking apparatus, even if the brightness of the eye to be examined greatly changes particularly at initial fluorescent state, the observation, the moving image recording, and the still image recording can be conducted at the appropriate gain with the appropriate light intensity. Thus, the appropriate image of the eye to be examined can be always obtained.

What is claimed is:

1. An ophthalmologic image taking apparatus comprising:
an illumination optical system that includes an observation illumination light source and an image taking illumination light source for illuminating an eye to be examined;

an image pickup unit for receiving a reflection light as an image of the eye to be examined from the eye to be examined;

an amplifying unit for amplifying an output signal from the image pickup unit;

a gain control unit for controlling a gain of the amplifying unit, the gain control unit having a first gain setting mode for changing the gain in accordance with the output signal from the image pickup unit and a second gain setting mode for setting the gain to a fixed gain;

a control unit for obtaining an output signal amplified by the amplifying unit as the image of the eye to be examined, the control unit having a first operational mode in which the output signal from the amplifying unit controlled in the first gain setting mode is continuously obtained and recorded on a record unit, and a second operational mode in which the output signal from the amplifying unit controlled in the second gain setting mode is obtained in synchronized with an emission of the image taking illumination light source and is recorded on the record unit as a still image; and a mode switch for switching between the first operational mode and the second operational mode of the image capturing unit, wherein the control unit determines a recording waiting time from switching to the first operation mode to starting of moving image recording.

2. An ophthalmologic image taking apparatus comprising:

an illumination optical system that includes an observation illumination light source and an image taking illumination light source for illuminating an eye to be examined;

an image pickup unit for receiving a reflection light as an image of the eye to be examined from the eye to be examined;

an amplifying unit for amplifying an output signal from the image pickup unit;

a gain control unit for controlling a gain of the amplifying unit, the gain control unit having a first gain setting mode for changing the gain in accordance with the output signal from the image pickup unit and a second gain setting mode for setting the gain to a fixed gain;

a control unit for obtaining an output signal amplified by the amplifying unit as the image of the eye to be examined, the control unit having a first operational mode in which the output signal from the amplifying unit controlled in the first gain setting mode is continuously obtained and displayed on a display unit, and a second operational mode in which the output signal from the amplifying unit controlled in the second gain setting mode is obtained in synchronized with an emission of the image taking illumination light source and is recorded on a record unit as a still image; and a mode switch for switching between the first operational mode and the second operational mode of the control unit, wherein the control unit determines an emission waiting time from a detection of turning-on of the mode switch to an emission of the image taking illumination light source.

3. An ophthalmologic image taking apparatus according to claim 1, further comprising observing unit for observing the image of the eye to be examined through the amplifying unit by using the observation illumination light source, wherein the control unit determines the emission waiting time based on an output result of the observing unit.

4. An ophthalmologic image taking apparatus according to claim 1, further comprising an observing unit for observing the image of the eye to be examined through the amplifying unit by using the observation illumination light source, wherein the control unit determines the moving image recording waiting time based on an output result of the observing unit.

5. An ophthalmologic image taking apparatus according to claim 1, wherein the illumination optical system comprises an exciter filter and an observation image taking optical system comprises a barrier filter, so that fluorescent observation image taking is possible.

* * * * *